(12) United States Patent
Warren

(10) Patent No.: US 6,362,481 B1
(45) Date of Patent: Mar. 26, 2002

(54) X-RAY DETECTOR APPARATUS WITH REDUCED THERMAL EXPANSIVITY

(75) Inventor: John M. Warren, Waukesha, WI (US)

(73) Assignee: General Electric Company, Waukesha, WI (US)

( * ) Notice: Subject to any disclaimer, the term of this patent is extended or adjusted under 35 U.S.C. 154(b) by 0 days.

(21) Appl. No.: 09/414,696

(22) Filed: Oct. 7, 1999

(51) Int. Cl.⁷ .................................................. G01T 1/20
(52) U.S. Cl. ............... 250/368; 250/361 R; 250/370.11
(58) Field of Search ........................... 250/368, 370.11, 250/361 R, 390.11

(56) References Cited

U.S. PATENT DOCUMENTS

| | | | | |
|---|---|---|---|---|
| 4,383,175 A | * | 5/1983 | Toepke | 250/368 |
| 4,421,671 A | | 12/1983 | Cusano et al. | 252/301.4 |
| 4,429,227 A | * | 1/1984 | DiBianca et al. | 250/367 |
| 5,521,387 A | | 5/1996 | Reinder et al. | 250/367 |

* cited by examiner

Primary Examiner—Huy Mai
(74) Attorney, Agent, or Firm—Jenkens & Gilchrist

(57) ABSTRACT

A technique is disclosed for providing a solid state X-ray detector for a CT imaging system with an optical coupler having a substantially reduced coefficient of thermal expansivity (CTE). In accordance therewith, a prespecified amount of a ceramic scintillator material, in powdered form, is mixed with the resin component of an optical coupling material, such as transparent epoxy, which has resin and hardener components. Air bubbles are removed from the powdered scintillator-resin mixture, and a prespecified amount of the hardener component of the optical coupling material is combined therewith to provide a powdered scintillator-optical coupler composite. The CTE of the composite is substantially less than the CTE of epoxy only. A monolithic block or body of the ceramic scintillator material is placed in close, spaced-apart relationship with a photodiode device, and the gap therebetween is filled with the reduced CTE optical coupler composite to eliminate air spaces therefrom.

19 Claims, 3 Drawing Sheets

X-RAY DETECTOR APPARATUS WITH REDUCED THERMAL EXPANSIVITY

BACKGROUND OF THE INVENTION

The invention disclosed and claimed herein generally pertains to an improved solid state X-ray detector which may be used in computed tomography (CT) diagnostic imaging systems, as well as for other applications. More particularly, the invention pertains to an X-ray detector of the above type which requires an optical coupler material. Even more particularly, the invention pertains to an X-ray detector wherein the optical coupler material is provided with a comparatively low coefficient of thermal expansivity (CTE).

As is well known in the art, solid state X-ray detectors are of increasing importance, for CT imaging and other applications. Such detectors generally include a monolithic block of polycrystalline ceramic scintillator material, which is positioned to receive a flux of X-radiation. The scintillator material may comprise, for example, a material sold by the General Electric Company, assignee herein, under the trademark Lumex, which is proprietary to GE. The X-ray energy received by the scintillator is converted, in proportion to its intensity, to near-visible light as it passes through the scintillator material. The light then excites a photo diode, which is located in close, adjacent relationship with the scintillator, and is designed specifically to convert the light into an electric signal suitable for processing by computer aided means.

In constructing an X-ray detector of the above type, it has been recognized that there must be no air gap or air space between the scintillator and the photo diode. Otherwise, some of the light generated by the scintillator would not be detected by the photo diode, due to light refractivity across the air gap. More particularly, the index of refraction for air is very different from the indices of refraction for the two detector components. As a result, some of the generated light could be reflected by the air-scintillator interface or by the air-photodiode interface, and thereby fail to reach the photodiode. Accordingly, to reduce such refractive losses, it has become common practice to place or sandwich an optical coupler between the scintillator and photodiode. The optical coupler is typically a transparent polymeric material (e.g., an epoxy) introduced as a liquid adhesive that solidifies and bonds the scintillator and photo diode together, and thus prevents any air spaces therebetween.

The above arrangement has generally proved effective in minimizing refractive losses, and thereby enhancing efficiency, in solid state X-ray detectors. However, a scintillator such as Lumex has a coefficient of thermal expansivity or CTE of approximately 6 PPM/° C., and a photo diode with a silica glass bonding surface has a CTE of approximately 7 PPM/° C. In contrast, an epoxy optical coupler of a type commonly used in the art can have a CTE as high as 200 PPM/° C. Such large mismatches in CTE can cause thermally induced strains at the optical coupler-scintillator and optical coupler-photodiode interfaces, which in turn may result in optical coupler detachment when the X-ray detector is exposed to temperature extremes. That is, as the X-ray detector experiences a large temperature change, dimensions of the optical coupler are likely to change by a much greater extent than dimensions of the scintillator and photo diode. Accordingly, the optical coupler may be subjected to substantial stress, and may even crack or become separated from other X-ray detector components.

SUMMARY OF THE INVENTION

The invention disclosed and claimed herein is directed to a comparatively simple and inexpensive technique for substantially reducing the coefficient of thermal expansivity of an optical coupler for a solid state X-ray detector, in comparison with the prior art. In one mode, the invention provides an X-ray detector apparatus which includes a first quantity of selected ceramic scintillating material, formed to comprise a monolithic scintillator body having a specified face. The scintillator body is disposed to receive an amount of X-radiation, and to project an amount of light corresponding thereto through the specified scintillator face. The detector apparatus further includes a photodiode device spaced apart from the specified scintillator face by a gap of selected width, the photodiode device being disposed to receive the projected light and to produce an electric signal which is proportional thereto, and is thereby proportional to or otherwise represent the amount of X-radiation received by the scintillator body. An optical coupling material of selected viscosity is positioned in the gap to reduce refractivity of light traversing the gap. A second quantity of the selected scintillating material, which is in the form of a powder, is mixed with the optical coupling material to provide an optical coupler composition of selectively reduced thermal expansivity.

Preferably, the scintillating material comprises a polycrystalline ceramic material such as Lumex which includes specified amounts of gadolinium oxide and a rare earth activator. In a preferred embodiment, the optical coupling material comprises a transparent epoxy material, and the X-ray detector is adapted for use in a CT imaging system. It is anticipated that an embodiment of the invention can provide an improved optical coupler for an X-ray detector having a CTE which is significantly lower than the CTE of an optical coupler conventionally used in solid state X-ray detectors.

In another mode, the invention is directed to a method for constructing an X-ray detector assembly for a CT imaging system. The method comprises mixing a prespecified amount of a ceramic scintillator material, in powdered form, with the resin component of an optical coupling material having resin and hardener components. Thereafter, air bubbles are selectively removed from the powdered scintillator-resin mixture. The method further comprises mixing a prespecified amount of the hardener component of the optical coupling material with the powdered scintillator-resin mixture to provide a powdered scintillator-optical coupler composite, and then removing air bubbles from the composite. A monolithic block or body of the ceramic scintillator material is placed in close, spaced-apart relationship with a photodiode device, to provide a gap of specified width therebetween, and the gap is filled with the composite to eliminate air spaces therefrom.

DETAILED DESCRIPTION OF THE PREFERRED EMBODIMENT

Figure 1:
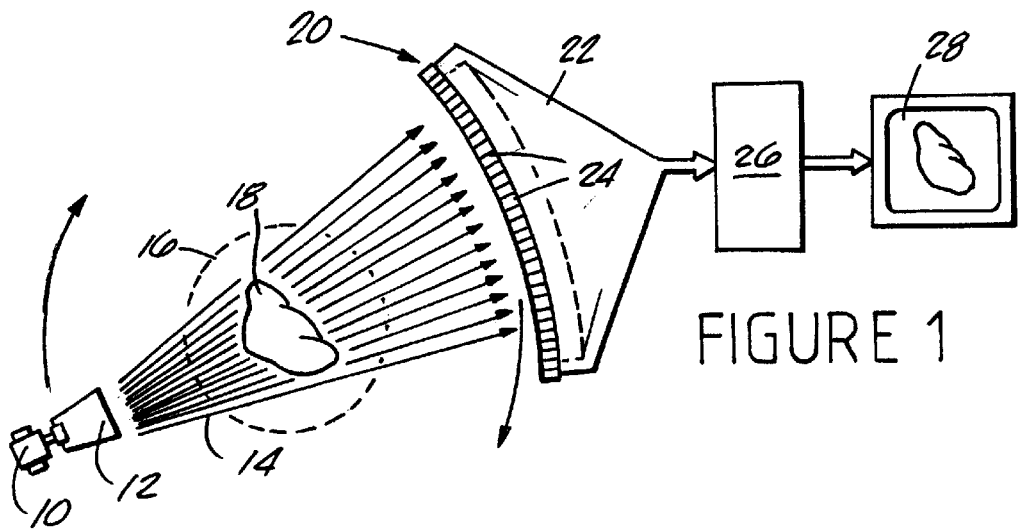
FIG. 1 is a schematic view depicting principal elements of a CT imaging system or scanner.

Referring to FIG. 1, there is shown the principal elements of a typical CT scanner used for the production, transmission and detection of X-ray radiation. The scanner includes a radiation source 10 for producing the radiation, which usefully comprises a rotating anode X-ray tube. Radiation produced by source 10 is collimated by a collimator 12 to produce a thin fan beam of X-rays 14, which is projected through aperture 16 toward a solid state X-ray detector array 20. A body to be examined, such as a patient or other subject 18, is positioned within the aperture 16 in the path of the X-ray fan beam 14. Accordingly, the beam is attenuated as it passes through the subject 18, the amount of attenuation being dependent upon the density of the body of the subject. Radiation detector array 20 comprises a detector array housing 22 having a plurality of detector cells 24. Detectors 24 are configured to receive respectively corresponding portions of the attenuated X-ray fan beam 14, and to produce electric signals which are proportional to or otherwise representative of the intensity of the radiation of the respectively received beam portions. The resulting electric signals are therefore measures of the attenuation of the X-ray beam by the respective portions of the body 18 through which the beam has passed.

In operation, electric signal readings are taken from each detector cell 24 at a plurality of angular positions with respect to subject 18, as the source 10 and the detector array 20 are being rotated about the aperture 16. The resulting readings are digitized and transmitted to a computer 26, which uses one of a number of available algorithms to compute and construct a picture of the cross section traversed by the fan beam of X-rays 14. The resulting picture is displayed on a cathode ray tube 28, or alternatively may be used to create an image on permanent media such as photographic film or the like.

Figure 2:
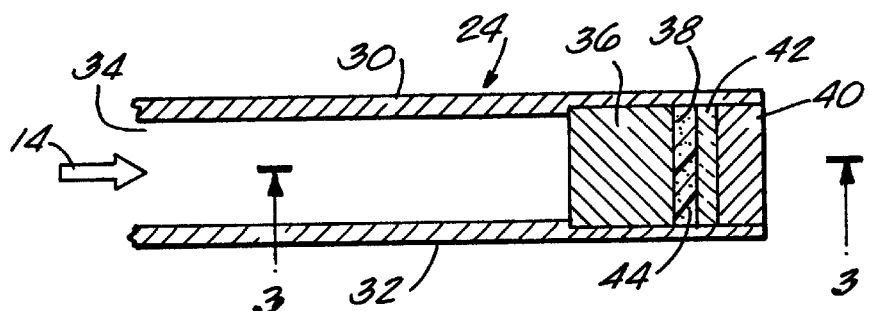
FIG. 2 is a sectional view schematically representing an X-ray detector cell for the CT scanner of FIG. 1, wherein the X-ray detector incorporates an embodiment of the invention.

In a solid state X-ray radiation detector array 20, each detector cell 24 typically is of the type schematically illustrated in FIG. 2. The detector width is defined by the distance between collimator plates 30 and 32, which collectively define a window for receiving X-rays 14 along an incremental portion of the fan beam which the detector 24 faces. As can be seen from a comparison of FIGS. 2 and 3, the detector cell width is considerably smaller than the length thereof, that is, the dimension of the detector which is perpendicular to the plane of the fan beam. It is desirable to minimize the detector width, in order to provide good spatial resolution of the fan beam. Typical detector cell dimensions in a practical radiation detector array may be on the order of one millimeter for the detector cell width and on the order of 20 millimeters for the detector cell length.

Referring further to FIG. 2, there is shown X-ray detector 24 provided with a polycrystalline ceramic scintillator body 36. Scintillator body 36 is disposed in a channel 34, which is defined by collimator plates 30 and 32 and comprises the space therebetween. Thus, X-ray radiation 14 received by channel 34 is incident on scintillator body 36 after passing between collimator plates 30 and 32. The incident radiation causes body 36 to scintillate at a predetermined wavelength, thereby converting the incident X-ray radiation into lower energy radiation in the visible or near-visible spectrum, i.e., into light energy. Accordingly, the X-ray detector 24 further comprises a device for detecting the visible spectrum or scintillator energy which is produced by scintillator body 36. Such device is coupled to the scintillator body 36 to produce an electric signal which is proportional to or otherwise represents the intensity of the X-radiation received by the scintillator body 36 through its corresponding channel 34 of the detector array 22. In the embodiment illustrated in FIGS. 2 and 3, the scintillator detecting device comprises a photodiode assembly 40, having an active surface 42. Surface 42, for example, may comprise a silica glass bonding surface. If the scintillator energy produced by scintillator body 36 is projected outward therefrom through a face 38, photodiode assembly 40 is positioned so that its active surface 42 is fixed in close, spaced-apart relationship with the scintillator body face 38. Photodiode 40 will thereby receive virtually all the scintillation radiation which body 36 produces in response to incident X-radiation.

Figure 3:
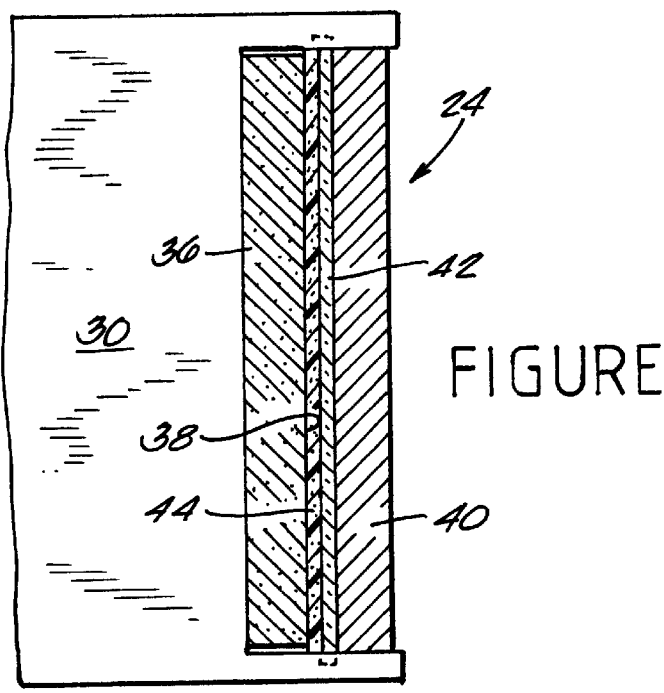
FIG. 3 is a sectional view taken along lines 3—3 of FIG. 2.

Various techniques are available for directing the light produced by scintillator 36 to active surface 42 of photodiode 40. For example, all the faces of scintillator 36, except for the face 38 thereof, may be treated to reflect inwardly any light which is incident upon the treated faces. Moreover, as shown in FIGS. 2 and 3, an optical coupler 44 is employed to fill the gap between face 38 of scintillator body 36 and active surface 42 of photodiode 40. The optical coupler 44 enhances coupling of light from the scintillator 36 to the photodiode 40 by substantially reducing refractive losses, as described above.

Scintillator body 36 could usefully be constructed from the material Lumex, referred to above. Lumex is similar or identical to a polycrystalline ceramic scintillator material disclosed in U.S. Pat. No. 4,421,671. The scintillator material disclosed therein is made up of rare earth yttria-gadolinia hosts and trivalent rare earth activator oxides. The scintillator composition may also include one or more of the transparency promoters and light output restorers described in such patent. A finished scintillator body, as described therein, is comprised of a cubic solid solution of the various chemical constituents. However, it is not intended to limit the scope of the invention to such scintillator material.

Figure 4:
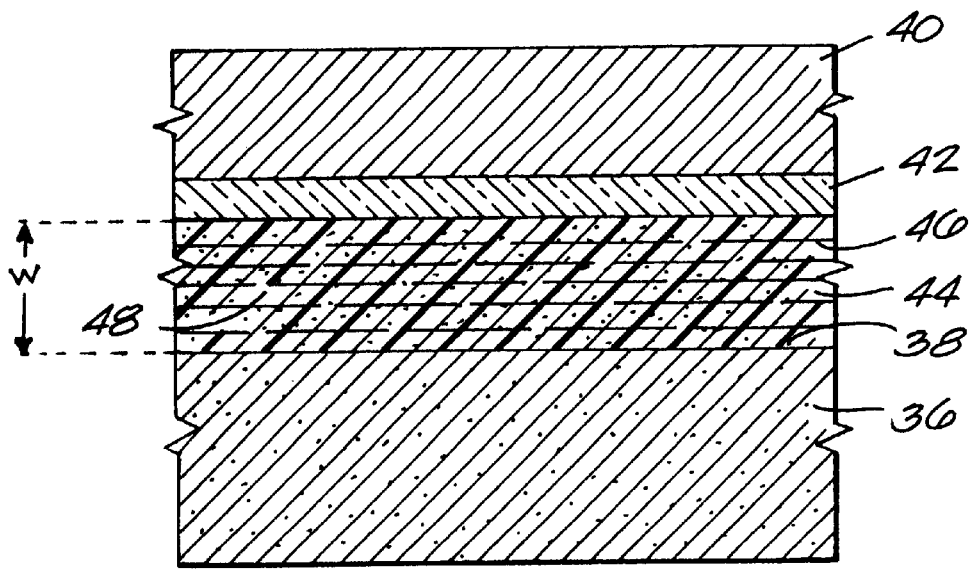
FIG. 4 shows a portion of FIG. 3 in greater detail.

Referring to FIG. 4, there is shown optical coupler 44 composition in greater detail, wherein such composition has been prepared in accordance with the invention. More particularly, optical coupler 44 includes a liquid adhesive, such as transparent epoxy 46, which solidifies and bonds scintillator body 36 and photodiode 40 together. In addition, FIG. 4 shows an amount of scintillator material 48, in powdered form, which has been mixed into epoxy 46. Scintillator material 48 preferably comprises the same scintillator material, such as Lumex, which is used to fabricate monolithic scintillator body 36, for example, by pressing and sintering powdered ceramic scintillator material into monolithic form.

It has been recognized that optical coupler 44, comprising a composition formed by mixing epoxy 46 and powdered scintillator material 48 together, in accordance with a procedure described hereinafter, has excellent optical coupling characteristics. Thus, the optical coupler composition 44 enhances transmission of light produced by scintillator body 36 from the scintillator body to photodiode 40, across the gap therebetween. At the same time, in accordance with the invention, it has been found that optical coupler composition 44 has a relatively low coefficient of thermal expansivity, in comparison with prior art optical couplers. For example, composition 44 may have a CTE that is approximately 50% of the CTE value of an unfilled epoxy typically employed for optical coupling applications. As a result, use of optical coupler composition 44 substantially reduces the effects of extreme temperature changes on the X-ray detector 24. It becomes much less likely that such temperature changes will strain the detector, and possibly damage it by detaching the optical coupler from the scintillator body or the photodiode.

In preparing optical coupler composition 44, the powdered scintillator material 48 is first sieved to a particular nominal size distribution, in order to accommodate the gap filling and size characteristics of the joint to be formed between scintillator body 36 and photodiode 40. Clearly the powder distribution must be smaller than the width of the gap being filled. Typically, the width w of the gap therebetween is on the order of 40–50 microns. Thereafter, the powdered scintillator material 48 is mixed with epoxy 46 by incorporating the scintillator material into the epoxy while the epoxy is still in the liquid state (i.e., prior to curing). More specifically, most commercially available epoxies manufactured for optical applications are made of two components, a hardener and a resin, which are mixed in specific proportions and subsequently heat cured. Incorporation of the scintillator powder 48 into the epoxy 46 is accomplished in several steps. First, a pre-weighed amount of scintillator powder is added to a pre-weighed quantity of resin and then thoroughly mixed to uniformly distribute the powder through the resin material. Respective proportions of the scintillator powder and resin may be determined by rule-of-mixture (ROM) analysis, as described hereinafter. Entrapped air bubbles are removed from such mixture by subjecting the mixture to a vacuum degassing operation. In vacuum degassing, the mixture is placed into an hermetic chamber, which is then evacuated by means of a vacuum pump.

In a second step, a pre-weighed quantity of hardener, measured in correct proportion to the resin, is added to the scintillator powder-filled resin, mixed, and as before, vacuum degassed. After the entrapped air bubbles are removed, the complete optical coupler composite system is ready for use in joining scintillator body 36 and photodiode 40.

Use of optical coupler composite 44 in an X-ray detector 24 provides a further benefit, in that the powdered scintillator material 48 in the optical coupler replaces an equivalent amount of non-scintillating epoxy material. It has been found that the scintillator characteristics of the powdered material 48 enhance overall efficiency of the detector 24.

In order to provide an optical coupler composition 44 which has a specified CTE, the rule-of-mixtures (ROM) may be employed to select the respective proportions of powdered scintillator material and epoxy for the composition. The ROM relationship is expressed as follows:

$$V_S \alpha_S + V_C \alpha_C = \alpha_T \quad \text{Eqn. (1)}$$

In Equation (1), $V_S$ is the volume fraction of powdered scintillator added to the epoxy coupler ($0 < V_S < 1$), $\alpha_S$ is the CTE (in ppm/° C.) of the scintillator material, $V_C$ is the volume fraction of the epoxy (equal to $1-V_S$), $\alpha_C$ is the CTE of the epoxy coupler and $\alpha_T$ is the resultant CTE of the composite mixture. The values of $\alpha_S$ and $\alpha_C$ must be applicable over the temperature range of interest. For example, if the joint between scintillator body 36 and photodiode 40 which is to be filled with the low expansivity coupler composite is exposed to a temperature range of −10° C. to 50° C., the values of $\alpha_S$ and $\alpha_C$ used in Equation (1) must also be valid over such temperature range.

The volume fraction values used in Equation (1) can be determined from the respective weights of the optical coupler composition components, multiplied by the specific volume v, using the following relationships:

$$V_S = (W_S v_S)/(W_S v_S + W_C v_C) \quad \text{Eqn. (2)}$$

$$V_C = (W_C v_C)/(W_S v_S + W_C v_C) \quad \text{Eqn. (3)}$$

$$W_T = W_S v_S + W_C v_C \quad \text{Eqn. (4)}$$

In Equations (2)–(4), $W_S$ is the weight (in grams) of the scintillator powder 48 in the composite mixture 44, $v_S$ is the specific volume of the scintillator powder (in m³/gram), $W_C$ is the weight of the epoxy coupler 46, $v_C$ is the specific volume of the epoxy coupler, and $W_T$ is the total weight of the two components in the mixture. Equations (1)–(4) can be solved simultaneously, to determine the volume fraction of scintillator powder 48 which is required to provide optical coupler composition 44 with a specified CTE.

The addition of scintillator powder to the epoxy coupler has practical limitations. The viscosity of the filled epoxy increases significantly with increasing Vs. Thus, at high values of Vs (i.e. >0.5) it might be desirable to modify the equipment used to apply the coupler, in accordance with practices well known in the art, to apply material of a type having a thick paste consistency.

Figure 5:
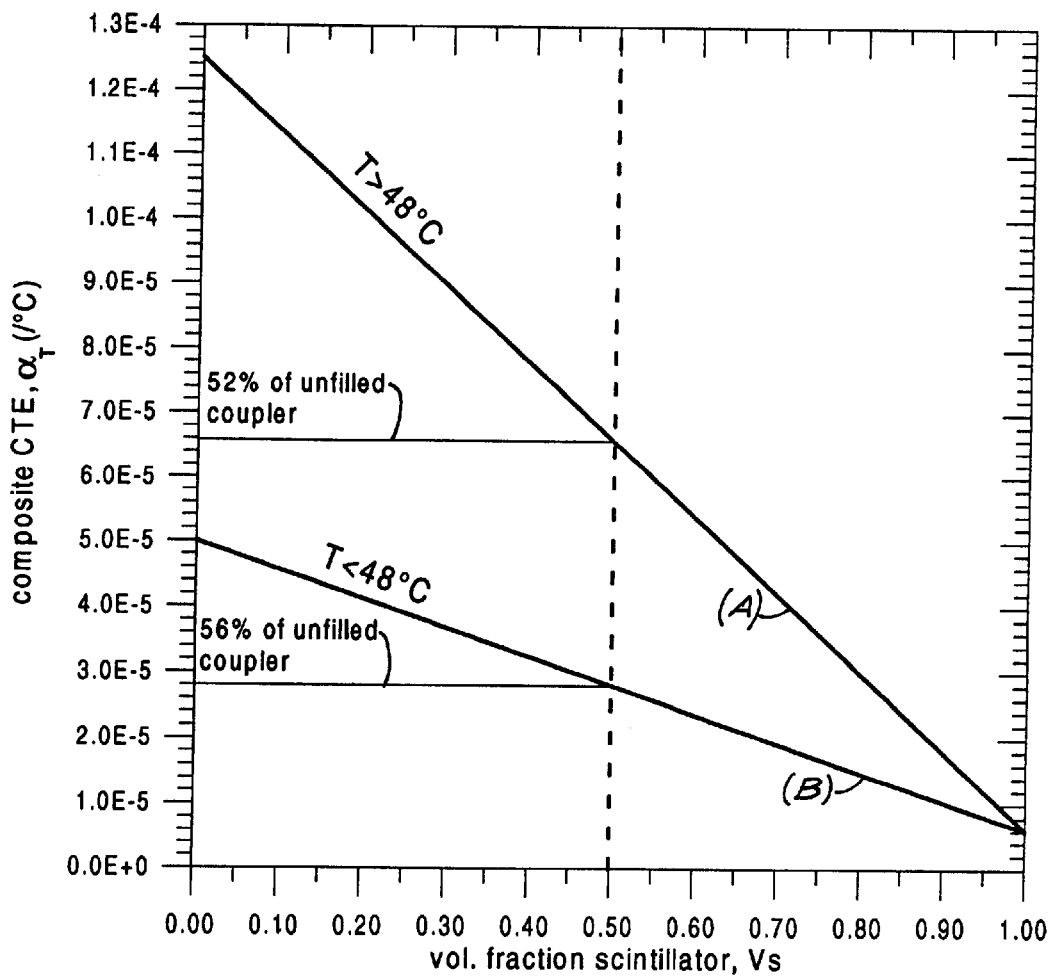
FIG. 5 is a plot of the CTE of a composition, formed in accordance with the invention, as a function of the volume fraction of a principal constituent material.

FIG. 5 is a plot of the resultant CTE of the composite mixture, $\alpha_T$, predicted by the ROM relationship of Equation (1), plotted as a function of the volume fraction Vs of scintillator powder 48. Equation (1) was solved using material parameters typical of optical couplers made from two-part epoxy resins. As is typical with these materials, the CTE increases significantly when the operating temperature exceeds a temperature referred to in the art as the glass transition temperature of the epoxy material. For the example shown in connection with FIG. 5, the glass transition temperature is 48° C. Hence, curve (A) of FIG. 5 is a plot of the predicted CTE for the composite mixture 44 for temperatures above the glass transition temperature. Similarly, curve (B) of FIG. 5 is a plot of the predicted CTE for the composite mixture 44 for temperatures below the glass transition temperature. The scintillator material properties are for the Lumex material described previously. The plots were generated using the following material parameters:

$\alpha_C = 50 \times 10^{-6}$/° C. for $T < 48°$ C. and $125 \times 10^{-6}$/° C. for $T > 48°$ $\alpha_S = 6 \times 10^{-6}$/° C. for all $T$ As shown in FIG. 5, for operating temperatures below 48° a scintillator powder fill of 50% by volume (0.50 $V_S$) lowers the CTE of $\alpha_T$ to about 56% of the value of the unfilled coupler 46. The CTE reduction above 48° C. is somewhat larger, with a resultant CTE of 52% of the unfilled coupler material 46.

Figure 6:
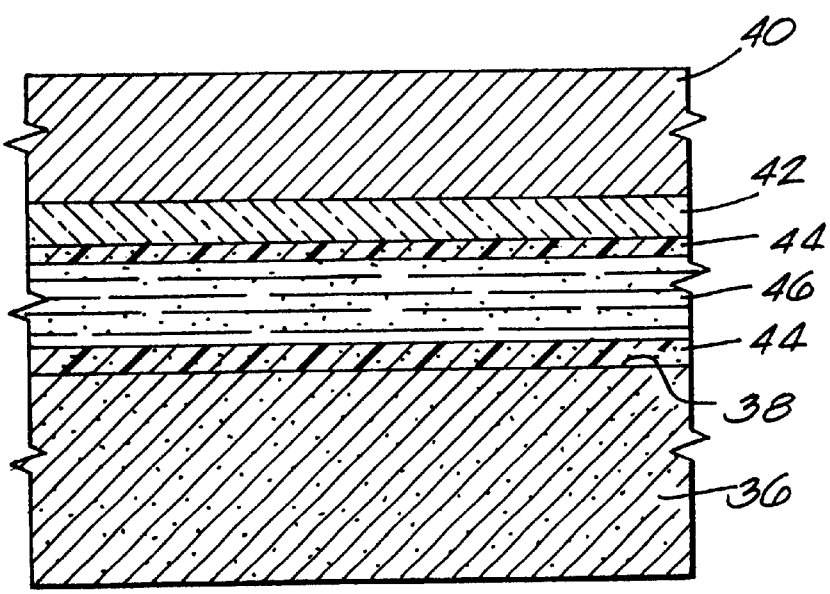
FIG. 6 is a sectional view showing X-ray detector components comprising a modification of the embodiment shown in FIG. 4.

Referring to FIG. 6, there is shown a modification of the invention, wherein a very thin layer of the optical coupling composition 44 is applied as a coating to the respective bonding surfaces of both the scintillator body 36 and the photodiode 40. A layer of conventional transparent epoxy 46 is then used to bond the two coated components together.

Obviously, many other modifications and variations of the present invention are possible in light of the above teachings. It is therefore to be understood that within the scope of the disclosed concept, the invention may be practiced otherwise than as has been specifically described.

What is claimed is:

1. X-ray detector apparatus comprising:
    a first quantity of polycrystalline scintillating material formed to comprise a monolithic scintillator body having a face, said scintillator body disposed to receive an amount of X-ray radiation, and to project an amount of light corresponding thereto through said face of said scintillator body;
    a photodiode device spaced apart from said scintillator face by a gap so that said photodiode device is disposed to receive said projected light, and to produce an electric signal representing said projected light and said X-ray radiation;

optical coupling material positioned in said gap to reduce refractivity of said projected light as said light traverses said gap; and a second quantity of said scintillating material, in the form of a powder, which is mixed into said optical coupling material to provide an optical coupler composition having a thermal expansivity which is substantially less than the thermal expansivity of said optical coupling material alone.

2. The apparatus of claim 1 wherein:

said scintillating comprises yttria-gadolinia and a rare earth activator.

3. The apparatus of claim 1 wherein:

said scintillating material comprises Lumex.

4. The apparatus of claim 2 wherein:

said optical coupling material comprises a transparent epoxy material.

5. The apparatus of claim 4 wherein:

said X-ray detector is disposed for use in a CT imaging system.

6. The apparatus of claim 1 wherein:

said scintillating material in said optical coupler composition comprises a volume fraction thereof which is functionally related to the coefficient of thermal expansivity of said composition.

7. In an X-ray detector provided with a solid state scintillator body formed of scintillating material, and further provided with a photodiode device spaced apart from said scintillator body by a gap, said scintillator body being disposed to receive X-radiation and to project an amount of light corresponding thereto across said gap to said photodiode device, an optical coupler composite disposed for insertion into said gap comprising:

a quantity of optical coupling material; and a quantity of said scintillating material, in the form of a powder, which is mixed into said optical coupling material to provide a composition having a thermal expansivity which is substantially less than the thermal expansivity of said optical coupling material alone.

8. The composition of claim 7 wherein:

said scintillating material in said optical coupler composition comprises a volume fraction thereof which is functionally related to the coefficient of thermal expansivity of said composition.

9. The composition of claim 8 wherein:

said scintillating material comprises yttria-gadolinia and a rare earth activator.

10. The composition of claim 8 wherein:

said optical coupling material comprises a transparent epoxy material.

11. A method for constructing an X-ray detector assembly for a CT system comprising the steps of:

preparing a mixture comprising an amount of a ceramic scintillator material in powdered form and a resin component of an optical coupling material;

mixing a hardener component of said optical coupling material with said powdered scintillator-resin mixture to provide a powdered scintillator-optical coupler composition; and placing a monolithic block of said ceramic scintillator material in close, spaced-apart relationship with a photodiode device to provide a gap therebetween, and filling said gap with said powdered scintillator-optical coupler composition.

12. The method of claim 1 wherein:

said method includes a preliminary step of sieving said powdered scintillator material to a particular nominal size distribution which is related to dimensions of said gap width.

13. The method of claim 12 wherein:

said step of preparing said powdered scintillator-resin mixture comprises adding an amount of said powdered scintillator material to a quantity of said resin, and then thoroughly mixing to uniformly distribute said powdered scintillator material through said resin.

14. The method of claim 13 wherein:

respective proportions of said powdered scintillator material and said epoxy coupler are determined by rule-of-mixture analysis.

15. The method of claim 14 wherein:

said powdered scintillator material in said composition comprises a volume fraction thereof which is functionally related to the coefficient of thermal expansivity of said composition.

16. The method of claim 15 wherein:

said powdered scintillator material includes amounts of yttria-gadolinia and a rare earth activator.

17. The method of claim 15 wherein:

said powdered scintillator material comprises Lumex, and said optical coupling material comprises transparent epoxy.

18. The method of claim 15 wherein:

said method includes the steps of removing air bubbles from said powdered scintillator-resin mixture, and from said composition.

19. The method of claim 18 wherein:

each of said air bubble removing steps is performed by means of a vacuum degassing operation.

* * * * *